(12) United States Patent
Hill

(10) Patent No.: US 7,062,972 B2
(45) Date of Patent: Jun. 20, 2006

(54) ACOUSTIC TRANSDUCER

(75) Inventor: James A. Hill, Haverhill, MA (US)

(73) Assignee: Horiba Instruments, Inc., Irvine, CA (US)

( * ) Notice: Subject to any disclaimer, the term of this patent is extended or adjusted under 35 U.S.C. 154(b) by 0 days.

(21) Appl. No.: 10/623,997

(22) Filed: Jul. 21, 2003

(65) Prior Publication Data

US 2005/0016281 A1    Jan. 27, 2005

(51) Int. Cl.
*G01N 29/00*    (2006.01)
(52) U.S. Cl. ...................................................... 73/632
(58) Field of Classification Search .................. 73/597, 73/629, 632, 644, 54.24, 54.41, 61.79, 64.53; 310/322, 328, 334
See application file for complete search history.

(56) References Cited

U.S. PATENT DOCUMENTS

| | | | |
|---|---|---|---|
| 4,297,607 A | 10/1981 | Lynnworth et al. | |
| 4,336,719 A | 6/1982 | Lynnworth | |
| 4,730,493 A * | 3/1988 | Lebaud et al. | ................ 73/599 |
| 4,743,870 A | 5/1988 | Jen et al. | |
| 4,783,997 A * | 11/1988 | Lynnworth | ................... 73/644 |
| 5,159,838 A | 11/1992 | Lynnworth | |
| 5,217,018 A | 6/1993 | Dias | |
| 5,241,287 A | 8/1993 | Jen | |
| 5,275,060 A * | 1/1994 | Lynnworth | ............... 73/861.18 |
| 5,355,048 A | 10/1994 | Estes | .......................... 310/334 |
| 5,438,999 A | 8/1995 | Kikuchi et al. | |
| 5,440,930 A * | 8/1995 | Daire et al. | ................... 73/644 |
| 5,756,360 A | 5/1998 | Harvey et al. | |
| 6,307,302 B1 | 10/2001 | Toda | |
| 6,343,511 B1 | 2/2002 | Lynnworth et al. | |
| 6,481,493 B1 | 11/2002 | Hielscher | ..................... 165/169 |
| 2002/0124662 A1 * | 9/2002 | Suzuki et al. | ............ 73/861.28 |

FOREIGN PATENT DOCUMENTS

| | | |
|---|---|---|
| DE | 10151992 | 5/2003 |
| JP | 2127897 | 10/1981 |
| JP | 2132327 | 5/1990 |

* cited by examiner

*Primary Examiner*—Hezron Williams
*Assistant Examiner*—Tamiko Bellmay
(74) *Attorney, Agent, or Firm*—Brooks Kushman P.C.

(57) ABSTRACT

An acoustic transducer includes an acoustic pulse generator, an impedance matching layer, and a thermal management system. The thermal management system is mounted to the matching layer to transfer heat from the matching layer, and is formed of a high thermal conductivity material relative to the matching layer. The thermal management system is arranged along the matching layer such that substantial heat is transferred to the environment from the thermal management system without excessive temperature increase at the pulse generator.

27 Claims, 3 Drawing Sheets

ACOUSTIC TRANSDUCER

BACKGROUND OF THE INVENTION

1. Field of the Invention

The present invention relates to acoustic transducers, including those used in flow meters.

2. Background Art

Transmitting pulses of acoustic energy through a fluid is useful for measuring the state and properties of the fluid, specifically the velocity and temperature. Piezoceramic elements are commonly used in acoustic transducers to generate ultrasonic acoustic pulses or continuous wave fields. However, these ceramics lose polarization if exposed to temperatures in excess of half of their Curie point. For commercially available ceramics, this limits the operating temperature of the ceramic to under 200° C. To operate in fluids above this temperature, one method is to provide a buffer or delay line between the piezoceramic element and the fluid (for example, exhaust gas) as shown in FIG. 1. FIG. 1 depicts an acoustic transducer 10. Transducer 10 includes piezoceramic element 12 and buffer 14 extending through wall 16 into the fluid which is illustrated as exhaust gas. Thermal energy is dissipated at internal convective boundary layer 18, in buffer 14, and at external convective boundary layer 20 as heat conducts upward in buffer 14 toward piezoceramic element 12. Buffers operate by the principle of Fourier's Law of heat conduction:

$$q'' = -\kappa \nabla T,$$

Where q" is the heat flux, κ is the thermal conductivity of the material and T is temperature. Detailed solutions of this equation require numerical methods but with some simplifying assumptions, a buffer system can be reduced to a lumped parameter model that can be represented as the equivalent circuit shown in FIG. 2. FIG. 2 illustrates the exhaust, buffer tip, crystal and ambient temperatures, and the thermal resistances of the external convective boundary layer, buffer, and internal convective boundary layer in a lumped parameter model.

For the lumped parameter model illustrated in FIG. 2, the temperature of the crystal is:

$$T_{crystal} = T_{exhaust} - (T_{exhaust} - T_{ambient}) \frac{(R_{IBL} + R_{buffer})}{R_{IBL} + R_{buffer} + R_{EBL}}.$$

A disadvantage associated with existing buffer systems is that a short buffer has problems when operating with hot fluids, while making the buffer longer requires that the buffer guide the wave front in the desired direction. However, solid buffers fail to effectively guide the acoustic pulse resulting in a dispersive buffer that distorts the ultrasonic pulse and limits the usefulness of the flow meter.

Additional background information may be found in U.S. Pat. Nos. 5,756,360; 4,336,719; 5,217,018; 5,159,838; 6,343,511; 5,241,287; 4,743,870; 5,438,999; 4,297,607; and 6,307,302.

For the foregoing reasons, there is a need for an improved acoustic transducer.

SUMMARY OF THE INVENTION

It is an object of the present invention to provide an acoustic transducer including a heat shielded acoustic matching coupler with integral cooling.

In carrying out the present invention, an acoustic transducer is provided. The transducer comprises an acoustic pulse generator, an impedance matching layer, and a thermal management system. The acoustic transducer is for measuring a property of a fluid. The impedance matching layer is between the pulse generator and the fluid. The matching layer is formed of a low thermal conductivity material. The thermal management system is mounted to the matching layer to transfer heat from the matching layer. The thermal management system is formed of a high thermal conductivity material relative to the matching layer. The thermal management system is arranged along the matching layer such that substantial heat is transferred to the environment from the thermal management system without excessive temperature increase at the pulse generator.

The acoustic pulse generator is preferably a piezoceramic element for generating an ultrasonic pulse. An impedance matching layer type of buffer is similar to a traditional buffer but has a reduced length to the point where traveling waves are no longer present and the dispersion problems associated with wave guides are not a concern. Put another way, the impedance matching layer is of small enough thickness that standing waves form. Preferably, the pulse generator is configured to operate at a particular frequency and the matching layer has a thickness approximately equal to an odd multiple of the quarter wavelength (λ/4, 3λ/4, 5λ/4, ...) of sound in the matching layer for the particular frequency of the pulse generator. Preferably, the matching layer thermal conductivity is less than 15 W/(m·K). More preferably, the matching layer thermal conductivity is less than 1 W/(m·K). The matching layer may be made of silica, and is preferably made of foam silica. Of course, ceramics or other materials may alternatively be used for the matching layer. By making the matching layer of a light weight, low thermal conductivity material that is more corrosion resistant than the body of the transducer, a metallic sealing layer is not needed and the matching layer may be in direct contact with the fluid which is being measured or have a light anti-reflective surface coating.

The thermal management system may vary in material and configuration provided that substantial heat is transferred to the environment from the thermal management system without excessive temperature increase at the pulse generator. Preferably, the thermal management system thermal conductivity is at least 15 W/(m·K). More preferably, the thermal management system thermal conductivity is at least 100 W/(m·K). The preferred thermal management system includes a plurality of fins mounted to the holder to dissipate heat low on the body of the matcher.

During operation, at least a portion of the matching layer sides and the matching layer tip extend into the fluid which is being measured. In a preferred implementation, the thermal management system is arranged to insulate the portion of the matching layer sides from heat from the fluid while leaving the tip of the matching layer in contact with the fluid. This may be achieved by insulating the portion of the matching layer sides with an air gap formed by the thermal management system. Further, in the preferred implementation, the thermal management system includes a sleeve over the matching layer to transfer heat from the matching layer.

Further, in carrying out the invention, an acoustic transducer is provided in combination with an apparatus including a conduit through which a fluid flows. The combination employs various features described above. The apparatus may be an exhaust gas sampling or testing apparatus.

Further, in carrying out the invention, a sampling system is provided. The system comprises a fluid inlet for receiving a fluid, a dilution inlet for receiving a dilution gas, a mixing section for mixing at least a portion of the fluid with the dilution gas, and a collection section for collecting a sample of the mixture. The system further comprises a flow meter for measuring a flow related to the sampling system. The flow meter includes an acoustic transducer for measuring the flow. The transducer employs various features described above. In one arrangement, the flow meter includes a pair of acoustic transducers arranged in an opposed fashion in a conduit through which fluid flows for measuring the flow.

Further, in carrying out the invention, a sampling system is provided. The system comprises a sample line for sampling a fluid from a main conduit, and a flow meter for measuring a flow of the fluid through the main conduit. The flow meter includes an acoustic transducer for measuring the flow. The system further comprises a dilution inlet for receiving a dilution gas, a mixing section for mixing the fluid flow from the sample line with the dilution gas at a generally fixed ratio, and a collection section for sampling the mixture. The mixture is sampled at a rate generally proportional to the flow of the fluid through the main conduit. The transducer employs various features described above. In one arrangement, the flow meter includes a pair of acoustic transducers arranged in an opposed fashion in the main conduit.

The advantages associated with embodiments of the present invention are numerous. For example, preferred embodiments of the present invention provide an acoustic transducer including a heat shielded acoustic matching coupler with integral cooling wherein the matching layer has a thermal management system mounted thereto such that substantial heat is transferred to the environment from the thermal management system without excessive temperature increase at the pulse generator.

The above object and other objects, features, and advantages of the present invention are readily apparent from the following detailed description of the preferred embodiment when taken in connection with the accompanying drawings.

DETAILED DESCRIPTION OF THE PREFERRED EMBODIMENT

Figure 1:
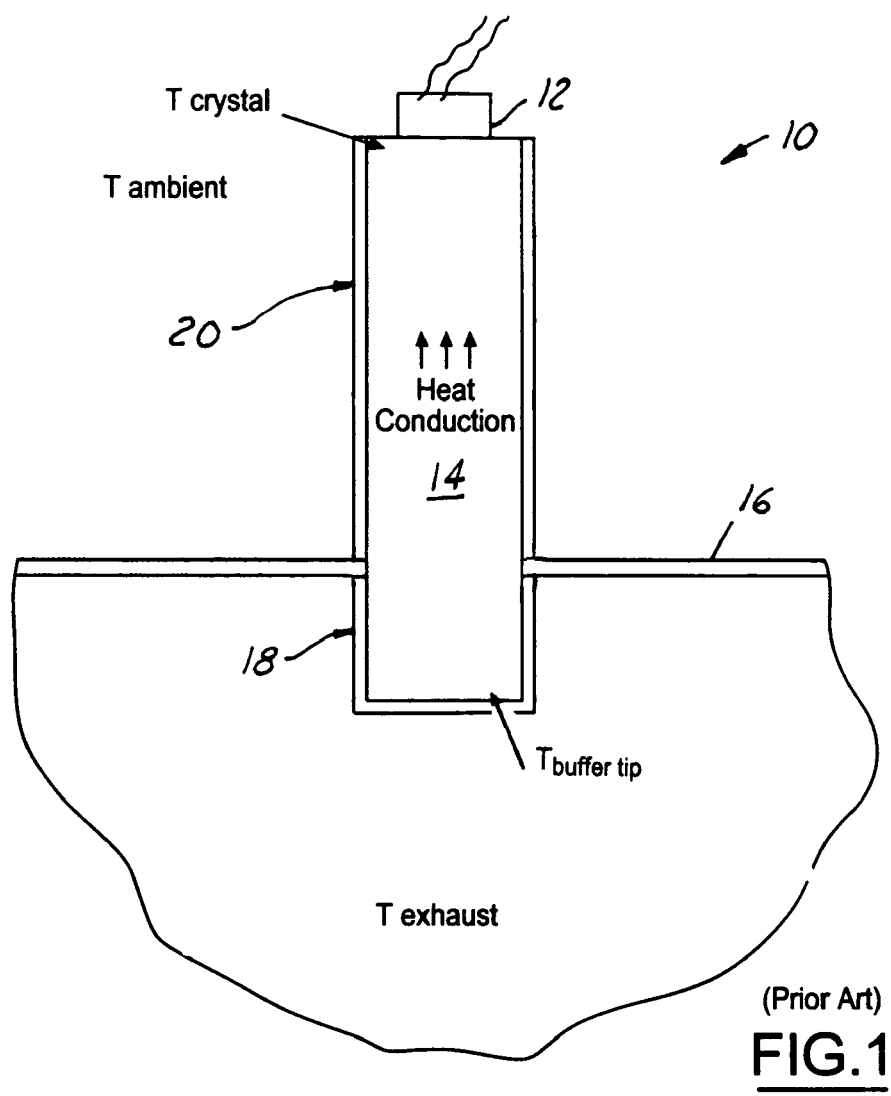
FIG. 1 illustrates a prior art use of a thermal buffer.
Figure 2:
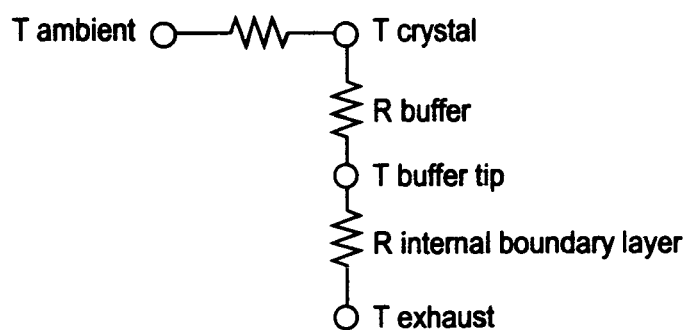
FIG. 2 illustrates an electrical equivalent circuit of the thermal buffer arrangement shown in FIG. 1.
Figure 3:
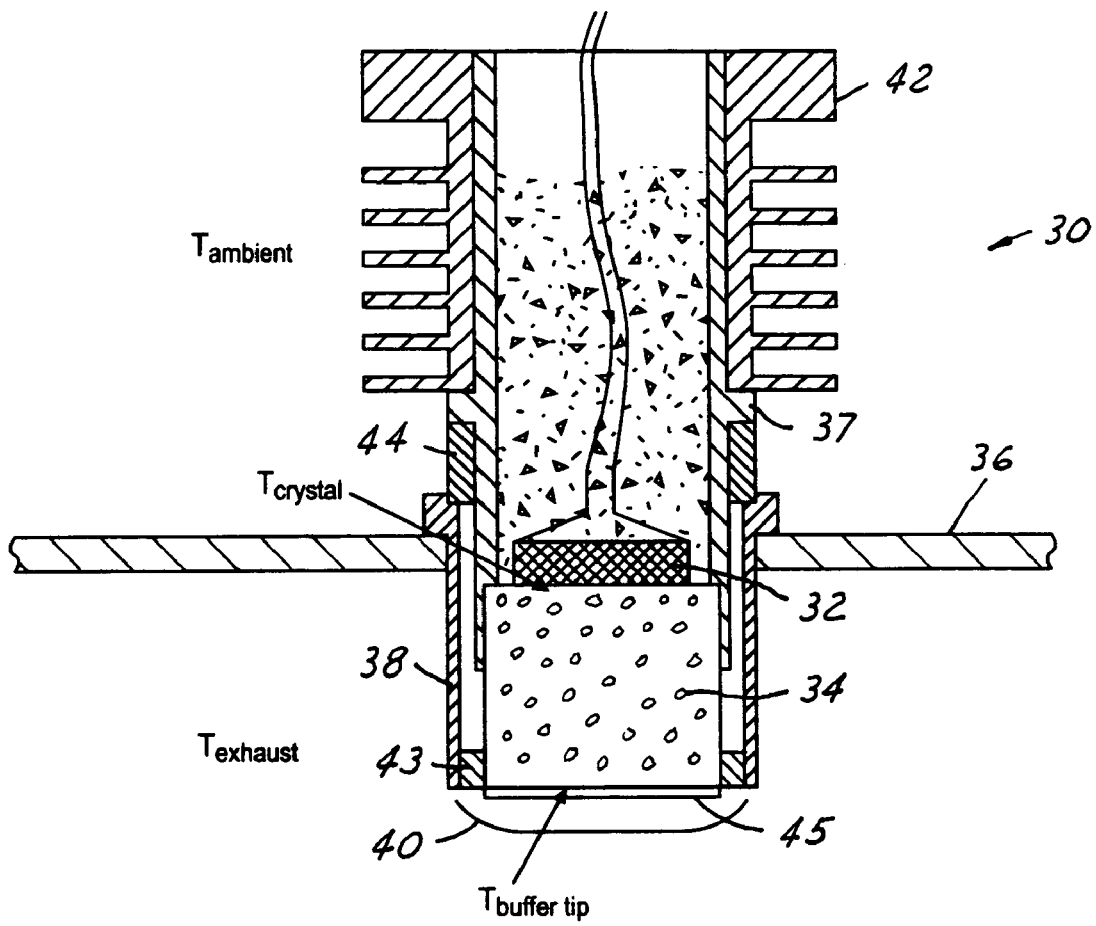
FIG. 3 illustrates an acoustic transducer in accordance with the present invention.

FIG. 3 illustrates an acoustic transducer 30 for measuring a property of a fluid. Transducer 30 includes piezoelectric element 32, and an impedance matching layer type buffer 34 which extends through wall 36 of a conduit through which the fluid flows. The conduit is part of an apparatus in which the acoustic transducer 30 is used. Impedance matching layer 34 is made of a light weight, low thermal conductivity material and is preferably foam silica. The impedance matching layer is of small enough thickness that standing waves form. The thickness should be an odd multiple of the quarter wavelength of sound in the matching layer for the particular frequency of the pulse generator. Transducer 30 also includes a thermal management system composed of a metal sleeve 37 over the matching layer 34 and piezoceramic element 32.

Figure 4:
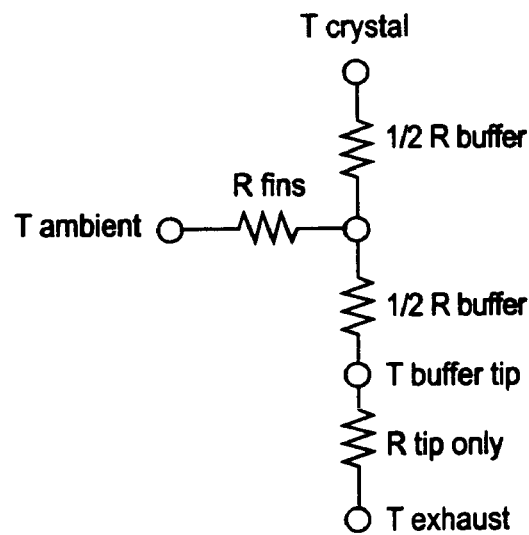
FIG. 4 illustrates an electrical equivalent circuit of the acoustic transducer arrangement shown in FIG. 3.

Sleeve 37 extends through wall 36 and a metal shield 38 with a small air gap between it and the matching layer 34 forms a high contact resistance in comparison to convective thermal boundary layer 40. The metal shield 38 also protects the buffer during installation and operation. The buffer tip is sealed to the metal shield 38 using a fired glass insert 43. The matching layer 34 may be coated with an anti-reflective coating 45 of an ultra-light material such as an aerogel to increase signal quality. Fins 42 are mounted to the sleeve 37 which holds piezoceramic element 32 to dissipate heat from low on the body of the matching layer 34. An epoxy seal bonds the sleeve 37 to the matching layer buffer 34 with minimal contact resistance to let heat flow freely through fins 42 of the thermal management system. An insulating ring 44 prevents direct heat transfer from shield 38 to sleeve 37 keeping the crystal at the same temperature as the sleeve 37. FIG. 4 with an electrical equivalent circuit illustrates the exhaust, buffer tip, crystal and ambient temperatures, and the thermal resistences of the buffer tip convective boundary layer 40, buffer 34, and fins 42. The buffer resistance is shown with part of the resistance before the fins 42 and part of the resistance after the fins 42 to model the dissipation of heat from low on the body of matching layer 34.

It is appreciated that the matching layer is formed of a low thermal conductivity material and the thermal management system is formed of a high thermal conductivity material and is arranged along the matching layer such that substantial heat is transferred to the environment from fins 42 without excessive temperature increase at piezoceramic element 32. That is, many variations may be made to the design while still achieving a suitable thermal management solution provided that the buffer remains small enough to function as an impedance matching layer and the thermal management system is mounted low enough on the matching layer. The matching layer materials and properties may vary depending on the configuration of other aspects of the thermal management system, for example, depending on the fin surface area.

Figure 5:
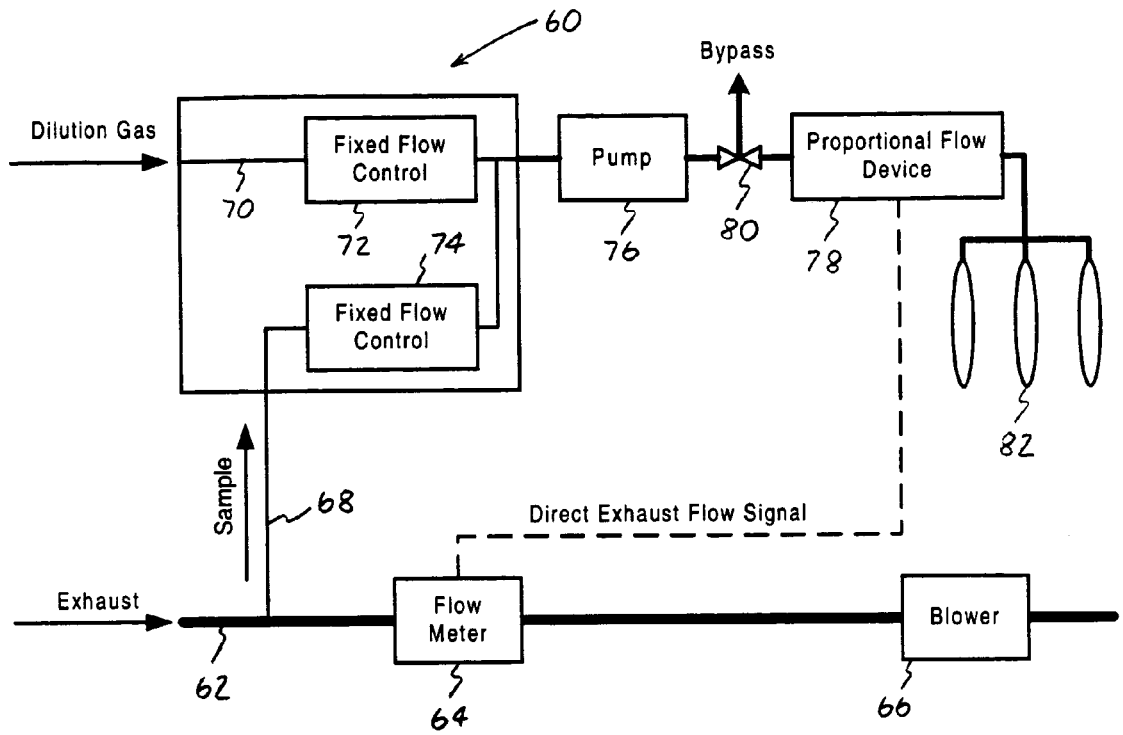
FIG. 5 illustrates a bag mini-diluter sampling system in accordance with the present invention.

FIG. 5 illustrates a bag mini-diluter sampling system at 60. Sampling system 60 includes a main conduit having an inlet 62 for receiving exhaust. Flow meter 64 measures the flow of fluid through the main conduit, and total exhaust volume is accumulated. Flow meter 64 provides a direct exhaust flow measurement signal, and includes at least one acoustic transducer of the present invention. Depending on the implementation, a blower 66 may assist fluid flow through the conduit.

A sample line 68 samples exhaust from the main conduit. A dilution inlet 70 receives a dilution gas. Fixed flow control 72 and fixed flow control 74 (mass flow controllers or critical flow venturis) control the flow of dilution gas and sampled exhaust gas, respectively, to provide a generally fixed ratio at the mixing section. Pump 76 pumps the mixture of the dilution gas and the exhaust gas sample for eventual collection in bags 82. Proportional flow device 78 provides a flow to sample collecting bags 82 that is proportional to the flow through the main conduit. Accordingly, bypass 80 is provided to allow some of the mixture to bypass the collections.

Figure 6:
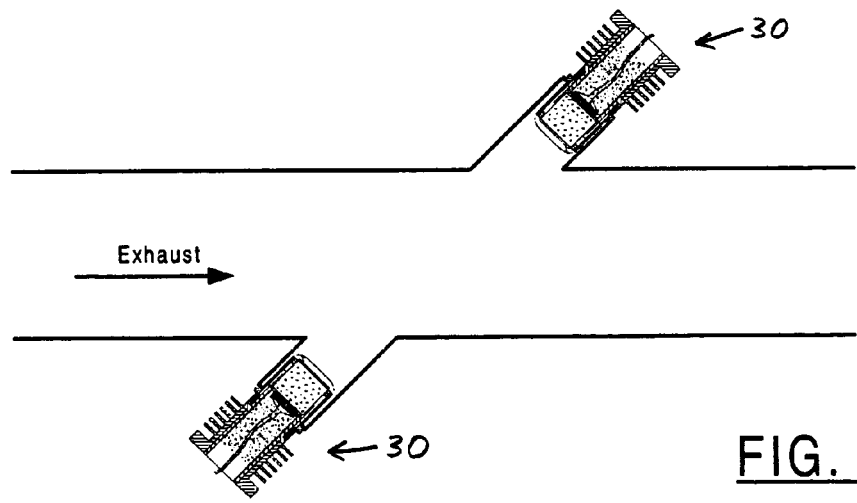
FIG. 6 illustrates the flow meter in the system of FIG. 5.

FIG. 6 illustrates flow meter 64 in greater detail showing a pair of acoustic transducers 30 arranged in an opposed fashion across the conduit.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An acoustic transducer for measuring a property of a fluid, the acoustic transducer comprising:
   an acoustic pulse generator;
   an impedance matching layer between the pulse generator and the fluid, the matching layer being formed of a low thermal conductivity material, the impedance matching layer having reduced length to the point where traveling waves are no longer present; and
   a thermal management system mounted to the matching layer to transfer heat from the matching layer, wherein the thermal management system is formed of a high thermal conductivity material relative to the matching layer and is arranged along the matching layer such that substantial heat is transferred to the environment from the thermal management system without excessive temperature increase at the pulse generator.

2. The acoustic transducer of claim 1 wherein the matching layer thermal conductivity is less than 15 W/(m·K).

3. The acoustic transducer of claim 1 wherein the matching layer thermal conductivity is less than 1 W/(m·K).

4. The acoustic transducer of claim 1 wherein the matching layer is made of foam silica.

5. The acoustic transducer of claim 1 wherein the matching layer is made of silica.

6. The acoustic transducer of claim 1 wherein the thermal management system thermal conductivity is at least 15 W/(m·K).

7. The acoustic transducer of claim 1 wherein the thermal management system thermal conductivity is at least 100 W/(m·K).

8. The acoustic transducer of claim 1 wherein the pulse generator is configured to operate at a particular frequency and wherein the matching layer has a thickness approximately equal to an odd multiple of the quarter wavelength of sound in the matching layer for the particular frequency of the pulse generator.

9. The acoustic transducer of claim 1 wherein the thermal management system includes a plurality of fins.

10. The acoustic transducer of claim 1 wherein the acoustic generator is a piezoceramic element for generating an ultrasonic pulse.

11. The acoustic transducer of claim 1 wherein the matching layer has a surface coating in contact with the fluid which is being measured.

12. The acoustic transducer of claim 1 wherein during operation at least a portion of the matching layer sides and the matching layer tip extend into the fluid which is being measured, and wherein the thermal management system is arranged to insulate the portion of the matching layer sides from heat from the fluid while leaving the tip of the matching layer in contact with the fluid.

13. The acoustic transducer of claim 12 wherein the insulated portion of the matching layer sides is insulated by an air gap formed by the thermal management system.

14. An acoustic transducer for measuring a property of a fluid, the acoustic transducer comprising:
    an acoustic pulse generator;
    an impedance matching layer between the pulse generator and the fluid, the matching layer being formed of a material with a thermal conductivity less than 1 W/(m·K); and
    a thermal management system including a sleeve over the matching layer to transfer heat from the matching layer, wherein the thermal management system is formed of a high thermal conductivity material relative to the matching layer and is arranged along the matching layer such that substantial heat is transferred to the environment from the thermal management system without excessive temperature increase at the pulse generator.

15. The acoustic transducer of claim 14 wherein the thermal management system thermal conductivity is at least 15 W/(m·K).

16. The acoustic transducer of claim 14 wherein the thermal management system thermal conductivity is at least 100 W/(m·K).

17. The acoustic transducer of claim 14 wherein the pulse generator is configured to operate at a particular frequency and wherein the matching layer has a thickness approximately equal to an odd multiple of the quarter wavelength of sound in the matching layer for the particular frequency of the pulse generator.

18. The acoustic transducer of claim 14 wherein the thermal management system includes a plurality of fins extending outwardly from the sleeve.

19. The acoustic transducer of claim 14 wherein the acoustic generator is a piezoceramic element for generating an ultrasonic pulse.

20. The acoustic transducer of claim 14 wherein the matching layer has a surface coating in contact with the fluid which is being measured.

21. The acoustic transducer of claim 14 wherein during operation at least a portion of the matching layer sides and the matching layer tip extend into the fluid which is being measured, and wherein the thermal management system is arranged to insulate the portion of the matching layer sides from heat from the fluid while leaving the tip of the matching layer in contact with the fluid.

22. The acoustic transducer of claim 21 wherein the insulated portion of the matching layer sides is insulated by an air gap formed by the thermal management system.

23. In combination with an apparatus including a conduit through which a fluid flows, the improvement comprising:
    an acoustic transducer for measuring a property of a fluid, the acoustic transducer including an acoustic pulse generator, an impedance matching layer, and a thermal management system, the impedance matching layer being between the pulse generator and the fluid, the matching layer being formed of a low thermal conductivity material, the impedance matching layer having reduced length to the point where traveling waves are no longer present, and the thermal management system being mounted to the matching layer to transfer heat from the matching layer, wherein the thermal management system is formed of a high thermal conductivity material relative to the matching layer and is arranged along the matching layer such that substantial heat is transferred to the environment from the thermal management system without excessive temperature increase at the pulse generator.

24. A sampling system comprising:
    a fluid inlet for receiving a fluid;
    a dilution inlet for receiving a dilution gas;
    a mixing section for mixing at least a portion of the fluid with the dilution gas;
    a collection section for collecting a sample of the mixture; and a flow meter for measuring a flow related to the sampling system, the flow meter including an acoustic transducer for measuring the flow, the acoustic transducer including an acoustic pulse generator, an impedance matching layer, and a thermal management system, the impedance matching layer being between the pulse generator and the fluid, the matching layer being formed of a low thermal conductivity material, and the thermal management system being mounted to the matching layer to transfer heat from the matching layer, wherein the thermal management system is formed of a high thermal conductivity material relative to the matching layer and is arranged along the matching layer such that substantial heat is transferred to the environment from the thermal management system without excessive temperature increase at the pulse generator.

25. The sampling system of claim 24 wherein the flow meter includes a pair of acoustic transducers arranged in an opposed fashion in a conduit through which fluid flows for measuring the flow.

26. A sampling system comprising:
    a sample line for sampling a fluid from a main conduit;
    a flow meter for measuring a flow of the fluid through the main conduit, the flow meter including an acoustic transducer for measuring the flow, the acoustic transducer including an acoustic pulse generator, an impedance matching layer, and a thermal management system, the impedance matching layer being between the pulse generator and the fluid, the matching layer being formed of a low thermal conductivity material, and the thermal management system being mounted to the matching layer to transfer heat from the matching layer, wherein the thermal management system is formed of a high thermal conductivity material relative to the matching layer and is arranged along the matching layer such that substantial heat is transferred to the environment from the thermal management system without excessive temperature increase at the pulse generator;
    a dilution inlet for receiving a dilution gas;
    a mixing section for mixing the fluid flow from the sample line with the dilution gas at a generally fixed ratio;
    a collection section for sampling the mixture, the mixture being sampled at a rate generally proportional to the flow of the fluid through the main conduit.

27. The sampling system of claim 24 wherein the flow meter includes a pair of acoustic transducers arranged in an opposed fashion in the main conduit.

* * * * *